United States Patent [19]

Adams et al.

[11] Patent Number: 5,449,377
[45] Date of Patent: Sep. 12, 1995

[54] OVERCHARGED FINAL COUNTERSHOCK FOR AN IMPLANTABLE CARDIOVERTER DEFIBRILLATOR AND METHOD

[75] Inventors: Theodore P. Adams, Edina; Mark W. Kroll, Minnetonka, both of Minn.

[73] Assignee: Angeion Corporation, Plymouth, Minn.

[21] Appl. No.: 125,288

[22] Filed: Sep. 22, 1993

Related U.S. Application Data

[63] Continuation-in-part of Ser. No. 856,982, Mar. 24, 1992, abandoned, which is a continuation-in-part of Ser. No. 33,632, Mar. 16, 1993, abandoned.

[51] Int. Cl.⁶ ............................................. A61N 1/39
[52] U.S. Cl. ............................................. 607/7
[58] Field of Search .............................. 607/5, 7, 8, 12

[56] References Cited

U.S. PATENT DOCUMENTS

| | | |
|---|---|---|
| 3,614,954 | 10/1971 | Mirowski . |
| 4,572,191 | 2/1986 | Mirowski et al. . |
| 4,708,145 | 11/1987 | Tacker, Jr. et al. . |
| 4,727,877 | 3/1988 | Kallok . |
| 4,800,883 | 1/1989 | Winstrom . |
| 4,953,551 | 9/1990 | Mehra et al. . |
| 5,107,834 | 4/1992 | Ideker et al. . |
| 5,178,140 | 1/1993 | Ibrahim . |
| 5,199,429 | 4/1993 | Kroll . |

FOREIGN PATENT DOCUMENTS 0280526  8/1988  European Pat. Off. .

OTHER PUBLICATIONS

Medtronic ® PCT TM Device Tachyarrhythmia Control System Reference Guide Apr. 1992.
Ventritex ® Cadence ® Tiered Therapy Defibrillator System Cadence Model V-100 and Cadence Programmer, Prel. Physician's Manual, Oct. 1990.
Ventak ® PRx TM 1700/1705 Physician's Manual, Cardiac Pacemakers, Inc.

*Primary Examiner*—William E. Kamm
*Assistant Examiner*—Scott M. Getzow
*Attorney, Agent, or Firm*—Patterson & Keough

[57] ABSTRACT

An implantable cardioverter defibrillator (ICD) device in operated in an overcharged final countershock condition so as to provide greater efficacy and broader treatment modality for the device. Instead of delivering a repeated series of up to five countershocks at the maximum rated charging voltage in response to a persistent ventricular arrhythmia as is done in existing ICD systems, an overcharged final countershock is delivered for which the electrolytic capacitor charge storage system of the ICD system is charged at a voltage that exceeds a maximum voltage specification. By delivering an overcharged final countershock, the present invention increases the chances of reversing a persistent ventricular arrhythmia which has become increasingly resistant to electrical therapy the longer the arrhythmia persists. As there is little to no risk in overcharging electrolytic capacitors for delivering the overcharged final countershock, and in fact the added electrical energy may overcome the increasing resistance to electrical countershock therapy, the present invention can deliver a more efficacious programmed therapy regimen than is available on existing ICD systems.

31 Claims, 10 Drawing Sheets

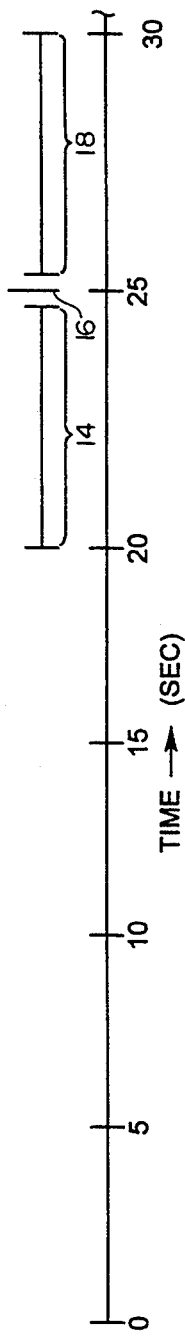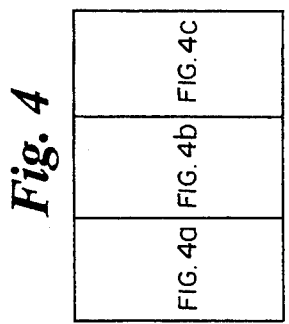
Fig. 1 PRIOR ART
Fig. 2 PRIOR ART
Fig. 4

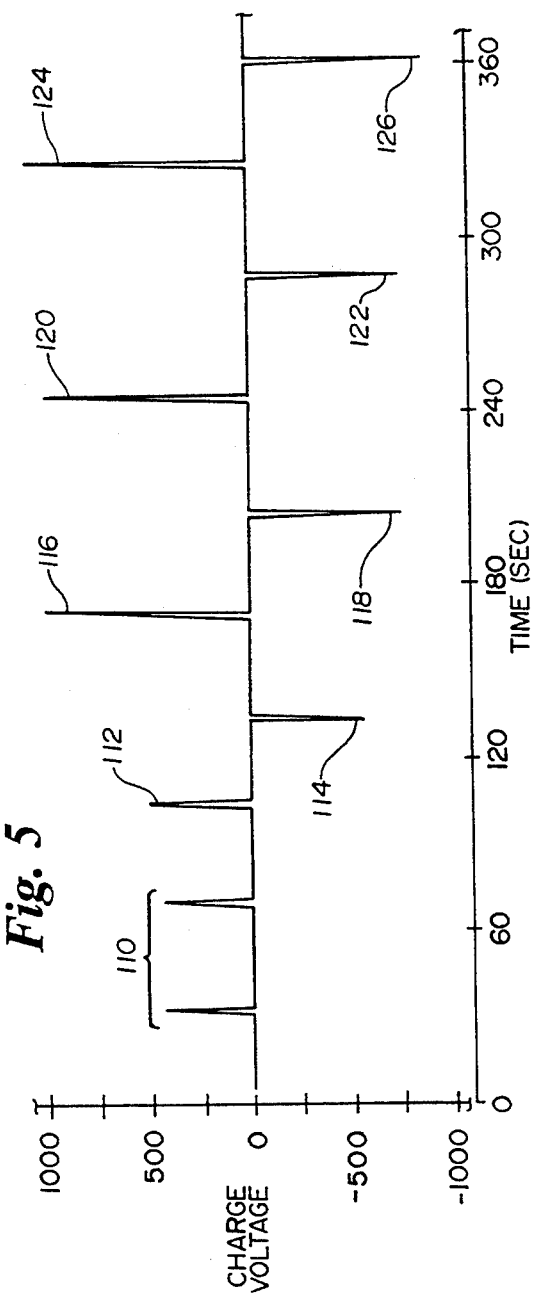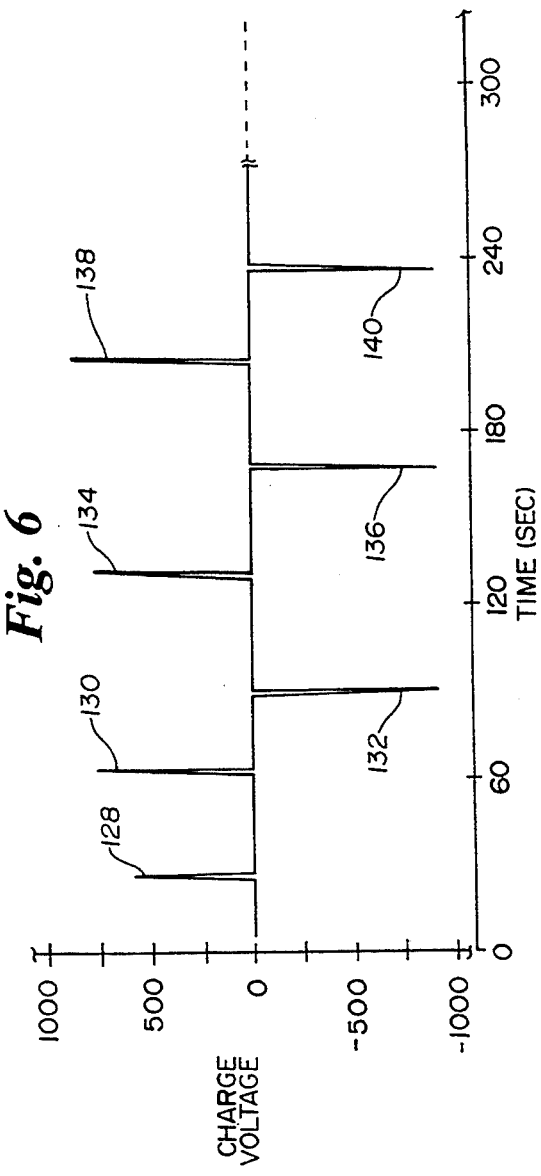

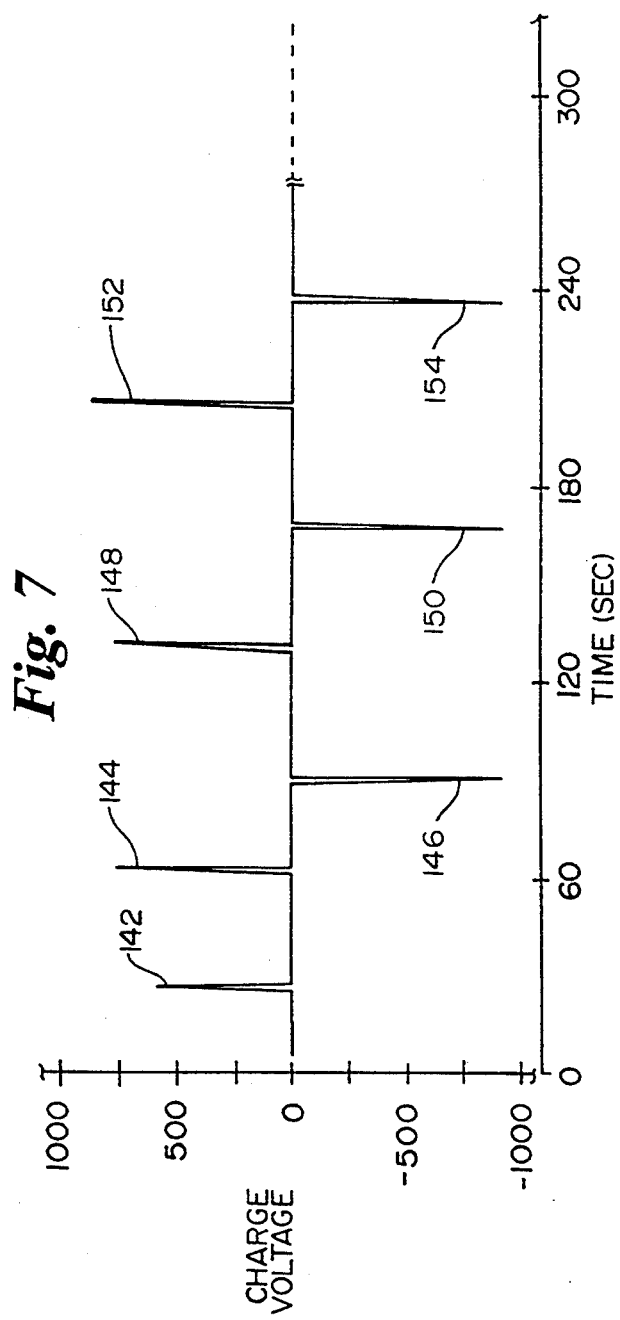

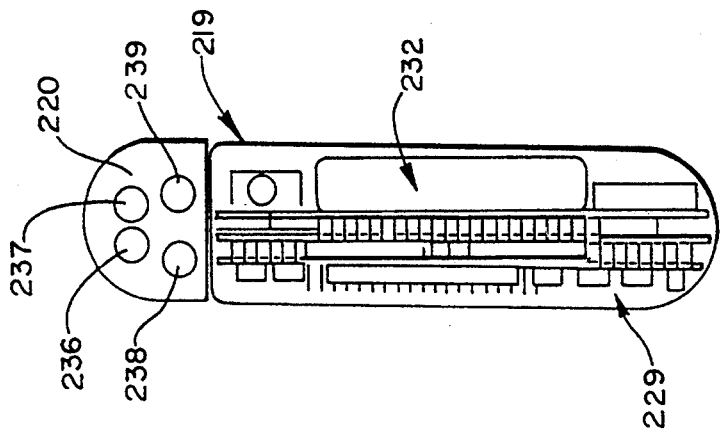
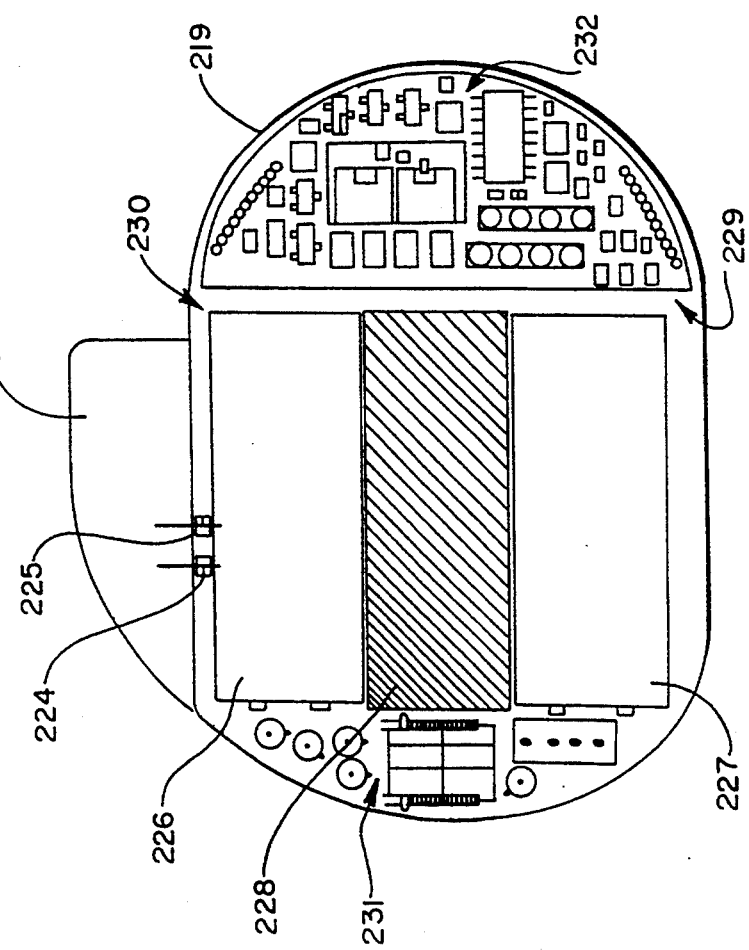

OVERCHARGED FINAL COUNTERSHOCK FOR AN IMPLANTABLE CARDIOVERTER DEFIBRILLATOR AND METHOD

RELATED APPLICATIONS

This application is a continuation-in-part of two prior applications filed in the United States Patent and Trademark Office, the first of which was filed on Mar. 24, 1992 and entitled SUCCESSIVE CHANGEABLE DEFIBRILLATION WAVEFORMS, U.S. patent Ser. No. 07/856,982; now abandoned, and the second of which was filed on Mar. 15, 1993 and entitled IMPLANTABLE CARDIOVERTER DEFIBRILLATOR HAVING A SMALLER DISPLACEMENT VOLUME, Ser. No. 08/033,632, abandoned both of which are assigned to the assignee of the present invention and the disclosure of each of which is hereby incorporated in the present application. A related co-pending application filed in the United States Patent and Trademark Office, was filed on Mar. 6, 1992, entitled FIBRILLATION AND TACHYCARDIA DETECTION, Ser. No. 07/848,147 and assigned to the assignee of the present invention.

FIELD OF THE INVENTION

The present invention relates generally to implantable cardioverter defibrillator systems and, more particularly, to an implantable cardioverter defibrillator capable of delivering an overcharged final shock in response to a persistent and potentially fatal ventricular arrhythmia.

BACKGROUND OF THE INVENTION

In most industrialized nations of the world, cardiac disease is the leading cause of death. Of the many deaths associated with cardiac disease, ventricular arrhythmia is a significant contributor to sudden death in this patient population. Fortunately, studies and work have shown that an otherwise fatal ventricular arrhythmia may be reversed with a timely delivery of a high voltage electrical shock, referred to as a countershock, to the myocardium of the heart in an attempt to restore, at least temporarily, the natural electrical rhythm of the heart.

As a background for understanding the present invention, it is helpful to understand the medical basis for why the electrical and muscular activity of the ventricles of the heart muscle can lead to the death of a patient. Ventricular arrhythmia have been described in several ways, but there are generally considered to be three types of ventricular arrhythmias: ventricular fibrillation, high rate ventricular tachycardia, and low rate ventricular tachycardia.

Ventricular fibrillation is described as the chaotic discharge of electrical and myocardial muscular activity dispersed throughout the ventricles that results in a mechanically non-functioning heart. Visually, ventricular fibrillation appears as if the myocardium were a mass of quivering worms. Onset of ventricular fibrillation results in instantaneous loss of cardiac output, as both blood pressure and perfusion pressures drop to zero. A patient so inflicted will lose consciousness within seconds and, if a perfusing pulse pressure is not reestablished within approximately three minutes, significant brain injury begins to occur that rapidly deteriorates to brain death within approximately five minutes.

Ventricular tachycardia is distinguishable from ventricular fibrillation on the basis of what appears to be an organized electrical activity of the myocardium. However, this electrical activity is so rapid that it exceeds the heart's ability to adequately pump blood. Cardiac output is dependent upon the degree of preload and filling the heart can achieve prior to the contraction event that produces the cardiac output. If the heart rate is too fast and exceeds the preload and filling time, the heart will have nothing to pump out. The end result of a high rate ventricular tachycardia can range from significantly lowered blood pressure and perfusion pressures to the absence of any pressures. Once again, a patient so inflicted will lose consciousness and, if the loss of perfusion pressure is significant, irreversible changes within the brain will occur due to loss of adequate oxygenation just as in the ventricular fibrillation scenario with permanent brain injury and ultimately brain death ensuing within minutes after onset of the high rate ventricular tachycardia.

Low rate ventricular tachycardia electrically appears very similar to the high rate ventricular tachycardia except for the slower electrical response time of the ventricles. Due to this lower rate, filling times are lengthened and some amount of blood is able to reach the ventricles in order to be pumped out on the next contraction cycle. The end result of low rate ventricular tachycardia is that the patient is able to sustain some blood pressure and perfusion pressure, but less than normal. Unfortunately, if a low rate ventricular tachycardia is allowed to persist it can, and most likely will, deteriorate to high rate ventricular tachycardia and ultimately ventricular fibrillation. A patient suffering from a low rate ventricular tachycardia may not be in imminent danger of dying, as are patients with ventricular fibrillation or even high rate ventricular tachycardia, but if there is not adequate intervention within minutes, the natural course of this disease process is to deteriorate to the more highly fatal arrhythmias.

Most people are familiar with the use of external defibrillators in an emergency situation where a patient with a ventricular arrythmia is treated by delivering a powerful electrical shock or countershock to the heart via external electrodes placed on the patient's chest. It should be noted that, while countershock therapy may prove efficacious in reversing the electrical arrhythmia portion of a ventricular arrhythmia, countershock therapy does not treat the underlying cardiac disease process that triggered the ventricular arrhythmia. Instead, countershock therapy provides a needed stopgap measure that allows additional time for medical responders to support a patient until further medical measures can be instituted to treat the underlying cardiac disease process.

More recently, implantable cardioverter defibrillators or ICD systems have been developed that automatically detect the onset of a ventricular arrhythmia and, in response, deliver a countershock to the myocardium via two or more implanted electrodes. Presently, there are several different ICD systems which have received device approval from the Federal Drug Administration, the PCD TM device, available from Medtronic, Inc., of Minneapolis, Minn., the Cadence ® device, available from Ventritex, Inc., of Mountain View, Calif., and the Ventak ® PRx TM device, available from Cardiac Pacemakers, Inc., St. Paul, Minn. These ICD systems have the obvious advantage of not requiring an emergency medical team with an external defibrillator in order to treat a patient with a ventricular arrythmia. In addition, because the electrical shock is delivered internally, rather than through the epidermal layer of skin, the electrical shock can be much less powerful and still perform its intended function.

The primary components of existing ICD systems include an automatic monitoring and detection mechanism, a capacitor system, a battery system and control circuitry for detecting a ventricular arrhythmia and controlling delivery of a high voltage capacitive discharge electrical countershock in response by charging and then discharging the capacitor system. The existing ICD systems are capable of delivering a maximum countershock of up to 700 to 750 volts having a total energy of between 31 to 44 joules. At the time an ICD system is implanted in a patient, the attending physician will empirically determine a minimum defibrillation threshold for the patient, and will program the charging voltages for the countershocks to be delivered as part of a therapy regimen within the range of maximum voltages allowed by the device.

In order to meet these discharge requirements while packaging the ICD systems within as small a container as is physically possible, design considerations must keep in mind the specifications on upper limits of size when making component choices. One such component that contributes significantly to the minimum size attainable by an ICD system is the capacitor system. The aluminum oxide electrolytic capacitor to date has proven to be the best capacitor technology for use in ICD systems. Due to the nature of the aluminum oxide dielectric, however, electrolytic capacitors are limited to maximum rated charging voltages in the range of approximately 350-375 volts. Beyond 375 volts, electrolytic capacitors begin to suffer from significant leakage current across the dielectric. This leakage current increases rapidly as the voltage is increased and charging of the electrolytic capacitor will cease when the leakage current equals the charge current. The advantage of electrolytic capacitors is that catastrophic breakdown due to overcharging is a rare event, the trade off being that an electrolytic capacitor cannot be charged beyond what the leakage current will allow. To that end, to maintain safe reproducible performance, present ICD systems utilize two electrolytic capacitors discharged in series to deliver the high voltage shock to the myocardium having a maximum voltage of approximately 700-750 volts.

By utilizing two electrolytic capacitors charged and then discharged in series, existing ICD systems avoid the disadvantage of wasted energy from leakage currents while still achieving the high voltage necessary to achieve successful defibrillation. This configuration also provides energy storage in as small a volume as is possible. It should be mentioned that other capacitor technologies and substantially higher voltages have been proposed in the prior art. For example, the original ICD patent, U.S. Pat. No. 3,614,945 issued to Mirowski proposed to charge a capacitor to 2,500 volts. This energy level is achievable using polymer film dielectric capacitor technology. With polymer films, a capacitor's voltage rating is proportional to the polymer film thickness. Consequently, such a capacitor charged to 2,500 volts would necessarily have a considerable and unmanageable volume and would not be suitable for use in a practical ICD system. In fact, no such implantable defibrillator system product has ever been developed using polymer film capacitors.

Existing ICD systems in general operate in accordance with the following functional steps. After implantation, the ICD system is in a monitoring mode, vigilant for the onset of a ventricular arrhythmia. If a ventricular arrhythmia is detected, existing ICD systems will generally follow a confirmation paradigm which lasts approximately five seconds to ensure that the initial detection is accurate. With confirmation, the existing ICD systems will begin charging the high voltage capacitor system to a preprogrammed voltage level to deliver an electrical countershock therapy for the detected arrhythmia. This process takes between 5-20 seconds depending on the energy setting and the battery capacity. Typically, for maximum voltage charges, the charging time is approximately 12-15 seconds. With completion of the charging, the diagnosis of a ventricular arrhythmia is typically reconfirmed, a process which can takes an additional 1-5 seconds. Following reconfirmation of a ventricular arrhythmia, the countershock is delivered. After countershock delivery, it can take anywhere from two and a half to ten seconds for the monitoring circuitry of the ICD system to settle down and restart the monitoring process to check for success or failure of the countershock therapy. Thus, the amount of time needed to deliver a single electrical countershock by existing ICD systems can take upwards of thirty or more seconds.

In the event that the countershock is not successful in reversing the cardiac arrhythmia, existing ICD devices repeat this cycle up to a maximum of five times. Depending upon the charging voltages programmed at the time of implantation, it is common that the first countershock of a therapy regimen will be programmed to deliver a voltage of less than about 700 volts and that the four subsequent countershocks of the therapy regimen will be delivered at the maximum rated charging voltage for the device. The reason why the first countershock may be programmed to be delivered at a lower voltage is that it has been shown that a countershock is more effective and requires less energy the earlier it is instituted in response to the detection of a cardiac arrhythmia. It will be seen that the limit of five countershocks per therapy regimen for existing ICD systems is in recognition of the fact that permanent brain injury begins to occur at approximately three minutes after onset of a lethal ventricular arrythmia. Existing ICD systems cannot practically deliver more than five countershocks in less than about three minutes.

Although existing ICD systems provide a useful mechanism for temporarily treating cardiac arrhythmias and thereby increase the survival chances of the patient, the existing manner in which the ICD systems are operated provides for an effective limit of five electrical countershocks per therapy regimen. Each countershock is delivered approximately every 30 seconds at a charging voltage not greater than the maximum rated charging voltage of the device. As a result, it is very common for physicians implanting the device to program the charging voltages for the second through fifth countershocks at the maximum rated charging voltage of the device. Unfortunately, the countershocks after the second or third countershock in this type of programmed therapy regimen have significantly less chance of success. For example, the fourth and fifth countershocks are identical to the preceding countershock, but are delivered at least 30 seconds later during which time the chances of the patient responding to electrical countershock therapy have continued to deteriorate.

Accordingly, it would be advantageous to provide an ICD system that could deliver a more efficacious programmed therapy regimen than the therapy regimens available on existing ICD devices. In addition, it would be advantageous if an ICD system could overcome the existing limitations imposed by the maximum charging voltages of electrolytic capacitor systems to further decrease the overall size of the ICD system.

SUMMARY OF THE INVENTION

The present invention provides a method and system for operating an implantable cardioverter defibrillator (ICD) device in an overcharged final countershock condition so as to provide greater efficacy and broader treatment modality for the device. The present invention recognizes that in response to persistent ventricular arrhythmia, the existing practice of delivering a repeated series of up to five countershocks at the maximum rated charging voltage has little chance of benefiting the patient because these countershocks are identical in charge level to countershocks that previously failed to treat the persistent arrhythmia. Termination of the series of five countershocks in existing ICD devices is a recognition that electrical therapy has failed and the ICD system is to give up, with the understanding that the patient has suffered a lethal cardiac event. The present invention acknowledges this logic and offers the insight that nothing is lost by delivering a final countershock for which the ICD system is charged at a voltage that exceeds the maximum rated specifications for charging the high voltage capacitor system. By delivering an overcharged final countershock, the present invention increases the chances of reversing a persistent ventricular arrhythmia which has become increasingly resistant to electrical therapy the longer the arrhythmia persists. As there is little to no risk in overcharging electrolytic capacitors for delivering the final countershock, and in fact the added electrical energy may overcome the increasing resistance to electrical countershock therapy, the present invention can deliver a more efficacious programmed therapy regimen than is available on existing ICD systems.

The present invention can be used to deliver high energy overcharged final countershocks in a conventional ICD system. The present invention can also be used to design an ICD system employing smaller components of lesser energy rating than has been the standard and thereby achieve an ICD system that is substantially smaller than existing ICD systems. The present invention achieves the same defibrillation threshold energy requirements with smaller capacitors by relying on an overcharged final countershock as part of a standard therapy regimen. An ICD system of smaller size carries the advantages of more flexibility in choosing the implantation site, the benefits of improved efficiency, shorter electrical leads, and so forth. Electrolytic capacitors can be overcharged from 5% to 15% above the rated maximum voltage for the capacitor before the leakage current begins to exceed the charging current. Therefore, the maximum amount of improvement to be gained can be as much as 10% to 25%, depending upon the degree of overcharging. This level of improvement is achievable because the energy of the delivered countershock is a function of the square of the discharge voltage. Even small increases in the discharge voltage can result in significant increases in the stored energy in the ICD system. As a result, the delivered energy for the final countershocks can be increased by this amount in an existing ICD system, or the ICD system size can be reduced by this amount, or the benefit can be shared between energy used and volume displaced.

While it would appear that the present invention might decrease, rather than increase, the ultimate safety and efficacy of an ICD device by operating the capacitor charging system beyond its maximum rated voltages, this is not the case. On the contrary, the present invention takes advantage of the nature of electrolytic capacitors not to fail catastrophically when charged beyond standard ratings. Typically, electrolytic capacitors have a maximum rated charging voltage below which leakage current is negligible. Beyond the maximum rated charging voltage, leakage current grows with increasing charging voltage. Unlike other types of capacitor technologies, however, there is no breakdown of the capacitor when it is charged above its maximum charging voltage. Instead, when the leakage current equals the charging current the electrolytic capacitor will not charge any further, and will remain in a steady state condition balancing the leakage current with the charging current.

There are several ways to monitor charging of the capacitor system in preparation for delivering an overcharged final countershock. One method simply specifies a charging time based on accurate knowledge of the capacitor properties. Another monitors the monotonically declining first derivative of the capacitor voltage, ending the charging cycle when the derivative has dropped to some preset value. A different method interrupts charging briefly and periodically to observe the leakage phenomenon by observing capacitor voltage decline. Still another method measures capacitor leakage directly by measuring voltage across a resistor connected between the capacitor and ground. Yet another approach is to simply program the ICD system to charge at an unconventionally high voltage, for example 800 volts or more, that is above the maximum programmable voltage of the device.

An object of the present invention is to provide an overcharged final countershock in a therapy regimen of an ICD system in such a manner that exceeds the standard capacitor voltage rating of the electrolytic capacitors of the ICD system.

Another object of the present invention is the application of an overcharged final countershock in a series of countershocks that is of a higher voltage than any of the preceding countershocks.

An additional object of the present invention is the delivery of an overcharged final countershock exceeding about 780–800 volts.

A still further object of the present invention is the realization of a reduction in the volume of an ICD system by increasing the energy of the final countershock capable of being delivered by smaller components.

Another further object of the present invention is to take advantage of the electrolytic capacitor proclivity for withstanding an overcharged voltage to secure a size advantage or an energy advantage or a combination of the two by departing from the conservative practice of limiting the maximum charging voltage of an ICD system to the nominal maximum voltage rating of the capacitor system.

These and other objects of the present invention as well as the advantages thereof will become more readily apparent when reference is made to the following description taken in conjunction with the accompanying drawings.

BRIEF DESCRIPTION OF THE DRAWINGS

FIG. 1 diagrammatically depicts an operational time line typical for existing ICD devices.

FIG. 2 diagrammatically depicts a conventional sequence of countershock outputs from existing ICD devices.

FIG. 5 is a diagrammatic representation of countershock output over time corresponding to the present invention's method approach for treating low rate ventricular tachycardia.

FIG. 6 is a diagram depicting the charge voltage output over time representative of the present invention's method for the treatment of high rate ventricular tachycardia.

FIG. 7 is a diagram depicting the voltage charge output over time for the treatment of ventricular fibrillation by the method of the present invention.

FIGS. 14 and 15 are side and frontal plan views, respectively, showing the power, capacitor, circuit and connector ports means positioned in the preferred embodiment of the ICD of the present invention.

DETAILED DESCRIPTION OF THE PREFERRED EMBODIMENT

Figure 3:
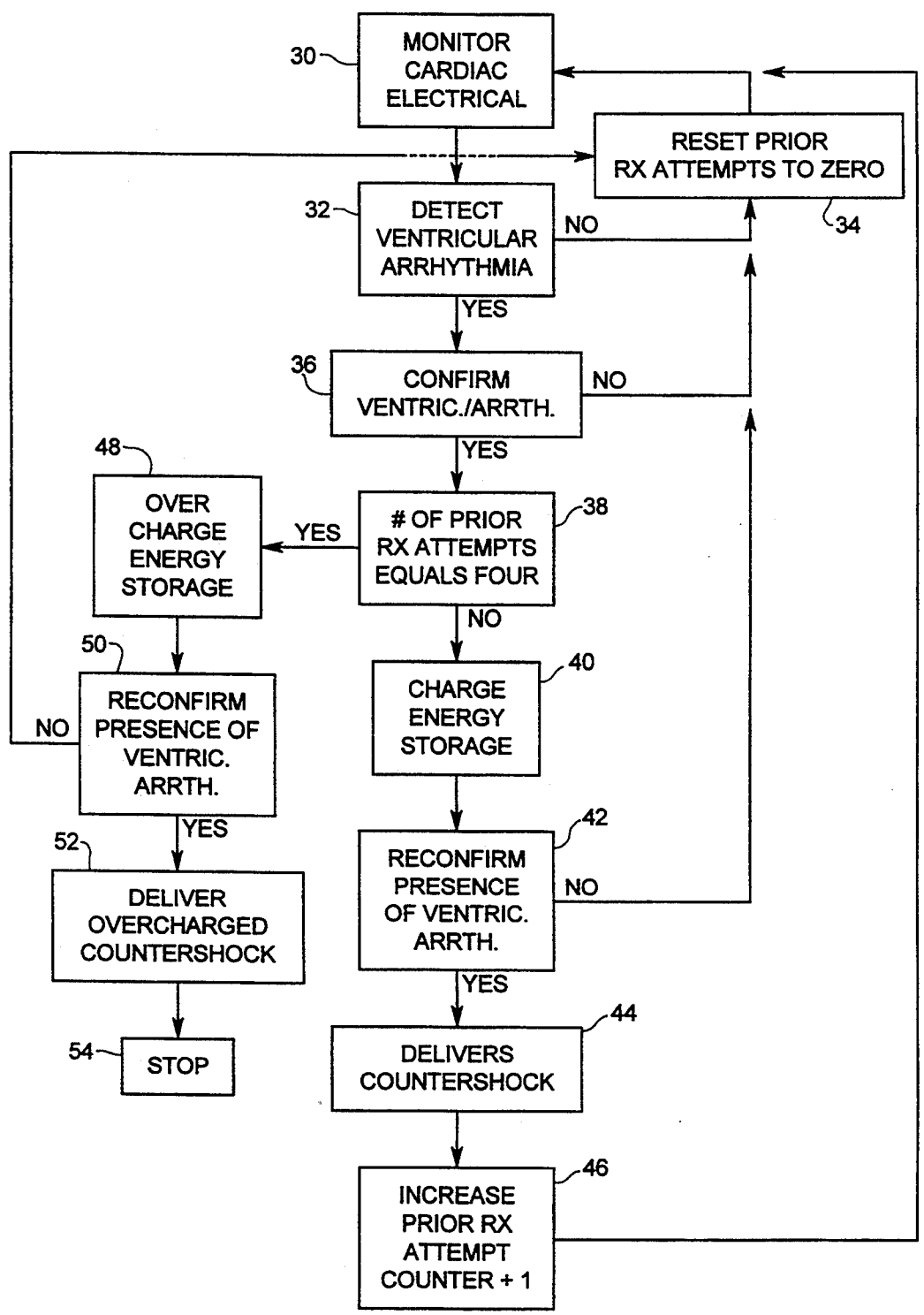
FIG. 3 is a flow diagram depicting a method application of a preferred embodiment of the present invention.

As briefly described above, in general, existing ICD devices take approximately 30 seconds to complete a cycle from detection of a ventricular arrhythmia to delivering a countershock to treat that ventricular arrhythmia. For a more detailed explanation of the operation of existing ICD devices, reference is made to the following publications: U.S. Pat. No. 4,800,883, issued to Winstrom, Jan. 31, 1989, entitled APPARATUS FOR GENERATING MULTIPHASIC DEFIBRILLATION PULSE WAVEFORM; U.S. Pat. No. 4,572,191, issued to Mirowski, et al., Feb. 25, 1986, entitled COMMAND ATRIAL CARDIOVERTER; *Medtronic ® PCD TM Device Tachyarrhythmia Control System Reference Guide*, Medtronic, Inc., April 1992; and *Ventak ® PRx TM 1700/1750 Physician's Manual*, Cardiac Pacemakers, Inc.

FIG. 1 depicts a conventional existing ICD device where time segment 10, lasting approximately 5 seconds, corresponds to the device's ability to detect and confirm the occurrence of a ventricular arrhythmia. Time segment 12 corresponds to the time period a device usually takes to charge to a full charge to deliver a maximum voltage discharge of the device. In FIG. 1, time segment 12 is shown as 15 seconds but this time period in practice can be as short as 10–12 seconds. Time segment 14 corresponds to that period of time a conventional device will devote to reconfirming the persistence of the ventricular arrhythmia. This reconfirmation serves as a safety check to prevent inadvertent or unnecessary electrical discharge of the ICD device. Time 16 refers to delivery of the countershock which is noted at two different positions in FIG. 1 depending upon the amount of time needed to reconfirm the presence of a treatable ventricular arrhythmia. Time segment 18 corresponds to that period of time conventional ICD devices require to recycle and get beyond the effects of delivering a high energy electrical countershock to the myocardium. Time segment 18 is variable in length depending upon the degree of built-in protection conventional ICD systems afford against the deleterious effects of inadvertent countershocks being shunted or shorted through the sensing electrodes of these devices. As shown in FIG. 1, on average, a single complete cycle from detection to treatment and resumption of function takes approximately 25–30 seconds, or longer.

As shown in FIG. 2, a series of countershocks is delivered over an approximately 180 second period for the treatment of persistent ventricular fibrillation. There are manufactured ICD systems available today, the PCD TM device, available from Medtronic, Inc., of Minneapolis, Minn., the Cadence ® device, available from Ventritex, Inc. of Mountain View, Calif., and the Ventak ® PRx TM device, available from Cardiac Pacemakers, Inc., St. Paul, Minn., all of which have received FDA approval as of August, 1993. All of these devices deliver a maximum of five high voltage countershocks to the heart. In all of these systems, the initial countershock delivered can be selectively programmed at the time of implantation to be of a lesser voltage than the maximum specified for that device. This is shown in FIG. 2 by countershock 20. This lowered voltage initial countershock helps to conserve energy to the ICD system because of the increased likelihood that successful countershock therapy will occur early on in the treatment course. However, if the fibrillating myocardium proves resistent to this initial lower energy countershock, the ICD system is then programmed to deliver a second countershock at maximum rated specified voltage. This is depicted at a countershock 22. If the fibrillating myocardium proves resistent to this treatment, conventional ICD systems will continue to repeat countershock 22 as part of the programmed therapy regimen until five complete countershock treatments have been delivered, after which the device will discontinue treatment even if ventricular fibrillation continues to persist. The cessation of treatment is accepted as a logical realization that, on the average, by the time conventional ICD systems have completed five countershocks, all of which are unsuccessful, the myocardium is beyond salvage and to persist is futile. A corollary line of reasoning for discontinuing treatment after five countershocks is a safety measure in the off-chance that the reason for the persistent detection of ventricular fibrillation is that the device is erroneously detecting ventricular fibrillation. If the device is an error, continued electrical countershocks occurring sequentially every 30 seconds can be extremely painful and detrimental to the point of causing fatality in an otherwise functioning myocardium.

In the preferred embodiment shown in FIGS. 11-15, the ICD system is of a smaller size than a conventional ICD system due to the use of a capacitor system having a smaller effective capacitance to deliver a lesser energy, but more effective, discharge countershock. While the preferred embodiment is described in connection with an ICD system having a smaller displacement volume, it will be understood that the present invention is equally applicable to larger, existing ICD systems. For a more detailed description of the operation of the ICD system of the preferred embodiment, reference is made to the previously identified co-pending application entitled IMPLANTABLE CARDIOVERTER DEFIBRILLATOR HAVING A SMALLER DISPLACEMENT VOLUME.

Figure 11:
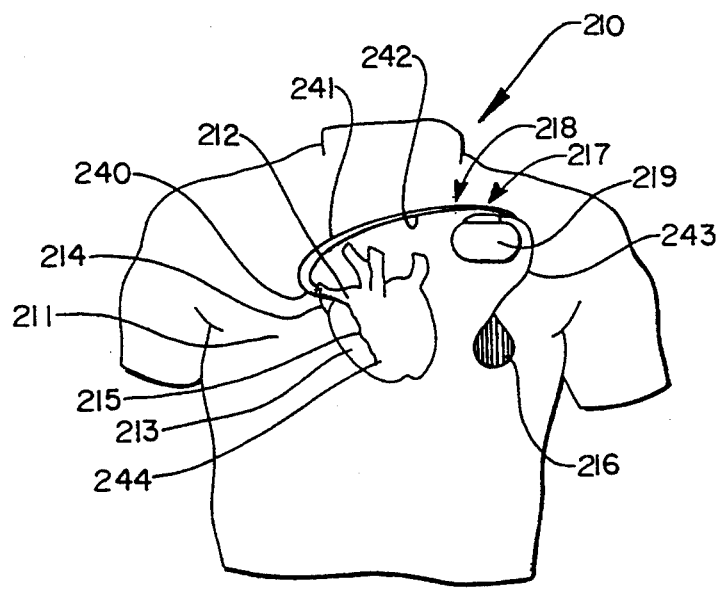
FIG. 11 is a frontal plan view showing the automatic, implantable cardioverter defibrillator of this invention implanted in the pectoral position of a human patient.

FIG. 11 shows a preferred embodiment of an ICD 217 of the present invention implanted in the pectoral region 218 of the chest 211 of patient 210. The ICD 217 has a plurality of connector ports for connection to various implantable catheter and other electrode means, as is known in the art. For example, electrode leads 241 and 242 are shown extending from ICD 217 to catheter electrodes 240 and 215 which are passed, respectively, into the superior vena cava 214 and the right ventricle 213 of heart 212. Further, lead 243 is shown extending from ICD 217 to a subcutaneous patch electrode 216. The specific configuration of the electrodes of the ICD system is dependent upon the requirements of the patient as determined by the physician.

Figure 13:
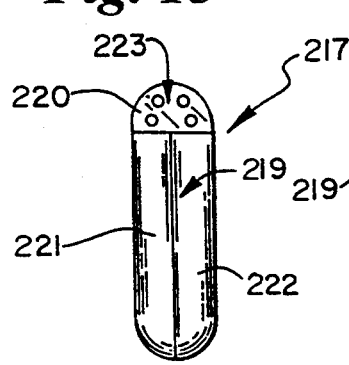
FIGS. 12 and 13 are frontal and side plan views, respectively, of the preferred embodiment of the ICD of the present invention.
Figure 12:
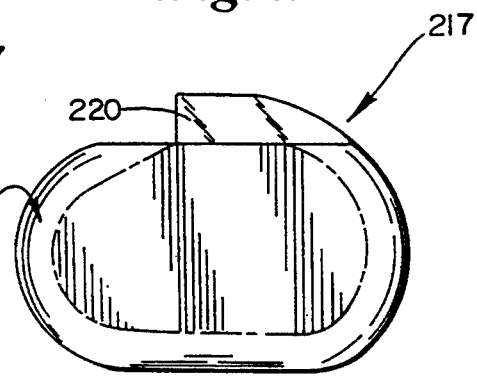

FIGS. 12 and 13 show ICD 217 comprised of a housing 219 having mating half shells 221 and 222. Positioned and mounted on top of housing 219 is a top connector portion 220 having a plurality of connecting ports 223 which are described further below. Importantly, ICD 217 is comprised of a compact, self contained structure having predetermined dimensions which permits pectoral implantation. In the preferred embodiment shown in FIG. 11, housing 219 is a compact and lightweight structure made of a biocompatible material and has a contoured configuration. The overall structure of this embodiment has a weight of less than 230 grams, and preferably less than 220 grams, and a volume of less than 90 cc, and preferably between about 40-80 cc. Housing 219 and top connector 220 are constructed and arranged to yield a cooperating structure which houses power means, control means and capacitive charge storage means. This cooperating structure permits subcutaneous implantation in the pectoral region of a human patient, provides a compact and effective ICD that automatically senses the bioelectrical signals of the heart and is able to provide a high voltage capacitive discharge to the heart for defibrillation purposes.

When selected in accordance with the optimized minimum physiological current ($I_{pc}$) as described in the previously identified co-pending parent application entitled IMPLANTABLE CARDIOVERTER DEFIBRILLATOR HAVING A SMALLER DISPLACEMENT VOLUME, the capacitor of ICD 217 has an effective capacitance of approximately 85 uF, and is constructed and arranged to deliver a maximum programmable discharge voltage of 750 Volts, for example. The maximum stored electrical energy for this arrangement is less than about 27 joules with an effective delivered defibrillation countershock energy of about 25 joules. In the preferred embodiment, the effective discharge voltage and capacitance is achieved by using two electrolytic photo flash-type capacitors in series, each having a capacitance rating of 170 $\mu$F and a maximum charging voltage rating of 375 Volts, while occupying a total displacement volume of only 7 cc each. The output of the capacitors is in communication with an electronic circuitry output portion that generally is comprised of a flash type circuit which delivers the capacitor discharge through electrodes 215, 216 and 240, for example.

FIGS. 14 and 15 show housing 219 having an interior space 230 wherein capacitors 226 and 227 are positioned and wherein a battery system 228 and circuit board portions 231 and 232 are positioned. Top connector 220 is shown mounted to the top of housing 219. Connecting ports 236, 237 and 239 are shown positioned in top connector 220. Connector ports 236 and 237 are connectable to the positive defibrillating electrode, for example, while connecting port 238 is connectable to the negative defibrillating electrode, for example, and connecting port 239 receives pacing/sensing electrode leads 241, 242. Channels 224 and 225 provide communicative and fastener members that provide for the attachment of top connector 220 to canister housing 219 and for the electrical connection between ports 236, 237, 238 and 239 and the electronic elements positioned in interior space 230 of housing 219.

Top connector 220 of ICD 217 has, for example, connecting ports 236 (DF+), 237(DF+), 238(DF−) and 239 (sensing/pacing). The lead connected to the DF− port, for example, is in conductive contact with catheter electrode 215 placed in the right ventricle 23 of the heart 212. The electrode lead(s) connected to the DF+ port(s) are connected to either or both of the electrodes positioned in the superior vena cava 214 and the subcutaneous patch electrode 216. Alternatively, the DF+ port holes may not be utilized, and plugged by a stopper means, for example, when the ICD body itself is utilized as the positive element to complete the defibrillation circuit. Pacing/sensing electrode 244 provides an input to connecting port 239 of ICD 217 and provides continual monitoring of cardiac signals from the heart 212. The circuitry of ICD 217 has means to detect any tachycardia or other arrhythmia condition and to thereby respond by the selective discharge of electrical energy stored in capacitors 226 and 227.

The shape of the countershock waveform used to treat the various cardiac arrhythmias can be monophasic, biphasic, multiphasic, reversed polarity and multiple combinations of the above. In general, ventricular fibrillation responds better to a biphasic wave than monophasic, where the opposite is generally the case for atrial fibrillation. A rectangular waveform is more efficacious than sinusoidal. For a more detailed discussion of countershock waveforms and treatment of cardiac arrhythmias, reference is made to IMPLANTABLE CARDIOVERTER DEFIBRILLATOR THERAPY: THE ENGINEERING-CLINICAL INTERFACE, edited by Mark W. Kroll, Ph.D., and Michael H. Lehmann, M.D., 1993.

FIG. 3 represents a flow diagram of the present invention's approach to treating ventricular arrhythmia. The embodiment depicted in FIG. 3 contemplates five consecutive electrical countershocks for persistent ventricular arrhythmia. However, the present invention further contemplates that, because the device will shut down following the fifth countershock and because fibrillating myocardium is increasingly resistant to electrical countershock therapy as time progresses, there is considerable advantage to overcharging the fifth countershock step in an all or nothing approach. As shown in FIG. 3, a monitoring step 30 determines the possibility of a ventricular arrhythmia and the device enters a logical detect step 32. If a ventricular arrhythmia is not detected, a reset step 34 resets a prior treatment attempt counter to zero and passes function back to step 30. If, on the other hand, logical detect step 32 returns a "yes", the function is passed to a logical confirm step 36 for confirmation of the presence of a ventricular arrhythmia. Once again, if confirmation determines that there is no ventricular arrhythmia, function is passed through step 34 back to step 30.

With confirmation of the presence of a ventricular arrhythmia at step 36, the present invention will query for the number of prior treatment attempts at step 38. As shown in step 38, if the number of prior treatment attempts does not equal 4, function is passed to step 40 and a normal maximum energy charge is triggered storing the energy in the high voltage capacitor. Once charging is complete there is reconfirmation at step 42. If reconfirmation determines the absence of a ventricular arrhythmia, function is returned through reset step 34 to monitoring step 30. Although not shown, the high voltage energy stored in the capacitor system would be drawn off of the high voltage capacitors as an unavoidable loss of energy.

Returning to reconfirmation step 42, if reconfirmation determines the continued presence of ventricular arrhythmia, the ICD system delivers a countershock as noted at step 44. Although the preferred embodiment of the present invention incorporates the reconfirmation step 42, it will be readily apparent that the present invention may also include a "committed shock" arrangement whereby the shock is delivered without confirmation step 42. Upon delivery of the countershock the prior treatment attempt counter is increased by one at step 46 and function is returned directly to step 30 to re-establish monitoring to determine success or failure of the countershock which was just delivered. The present invention will cycle through these steps until arriving at step 38 when the number of prior treatment attempts equals four and a logical "yes" is returned. The system passes function to an overcharge step 48 allowing for overcharging the high voltage capacitor system in preparation for a final countershock. When charging is complete, function is passed to step 50 for reconfirmation of the presence of a ventricular arrhythmia. Once again, if it is determined that a ventricular arrhythmia is not present, the device function is returned to step 34 to reset the prior attempts counter to zero and return to a monitoring function at step 30. If step 50 returns a logical "yes" indicating the presence of ventricular arrhythmia, the device will deliver an overcharge countershock at step 52. Following this overcharge countershock the device then moves to step 54 and stops.

Figure 4A:
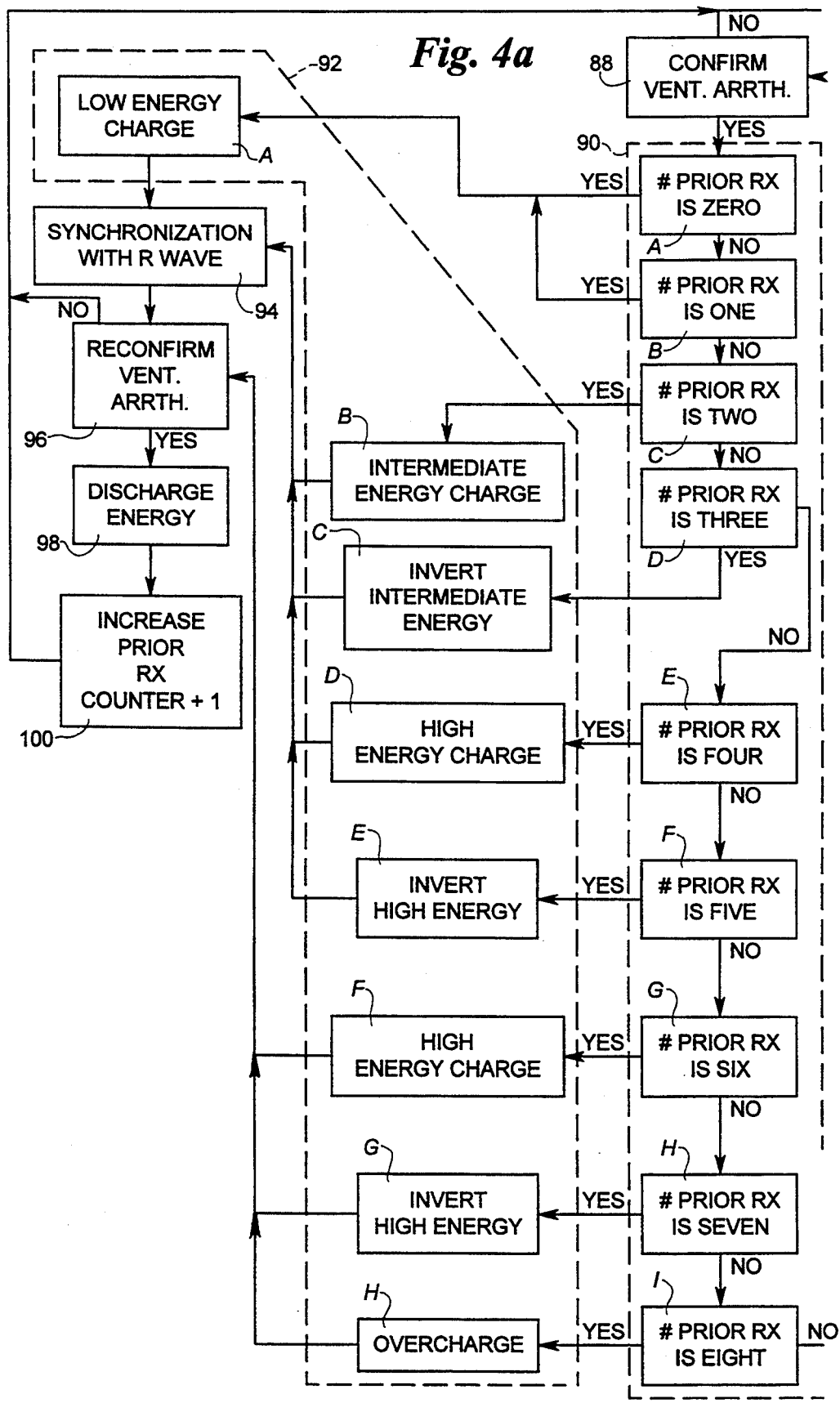
FIGS. 4A–4C are flow diagrams depicting an additional embodiment of the present invention.
Figure 4B:
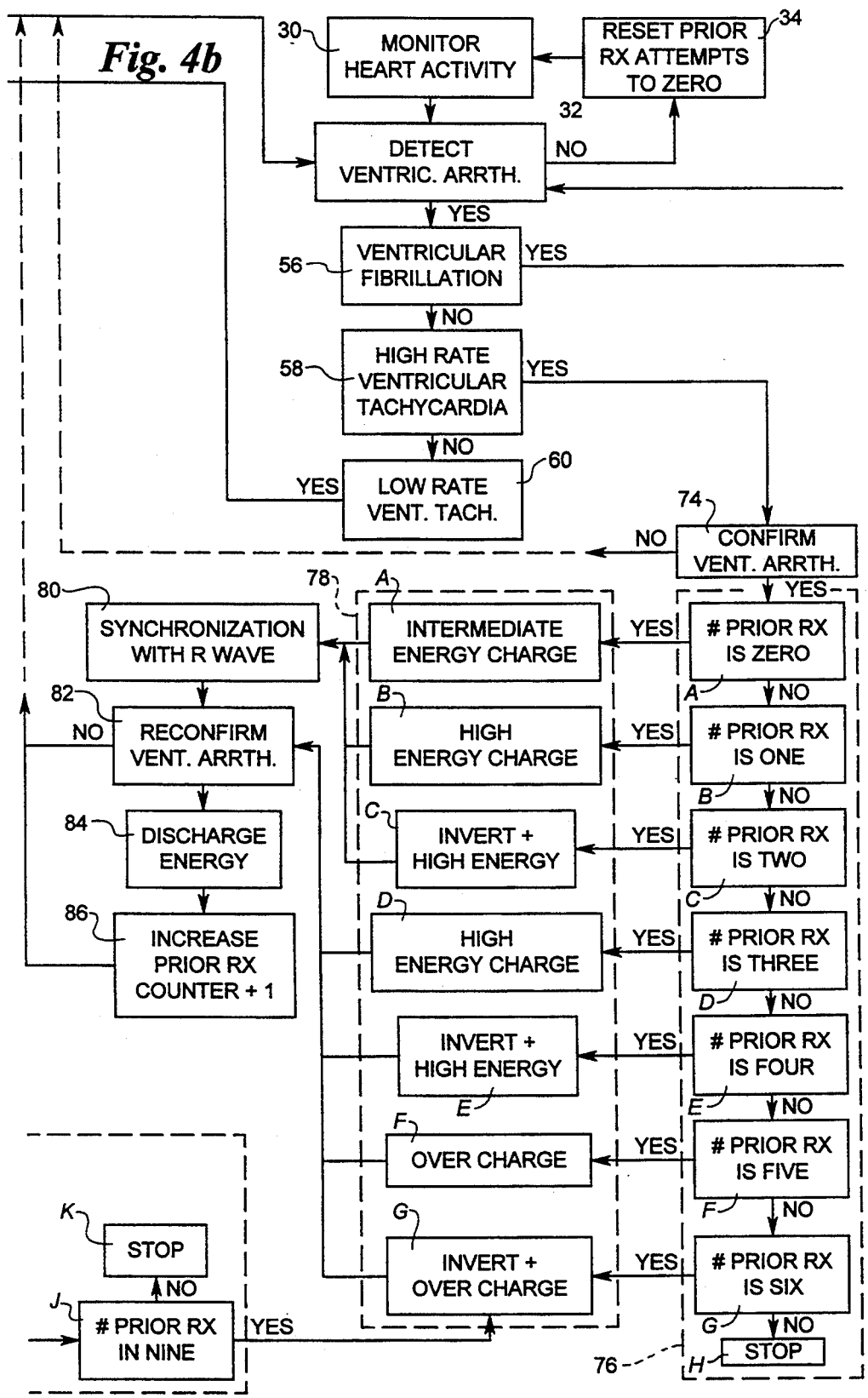
Figure 4C:
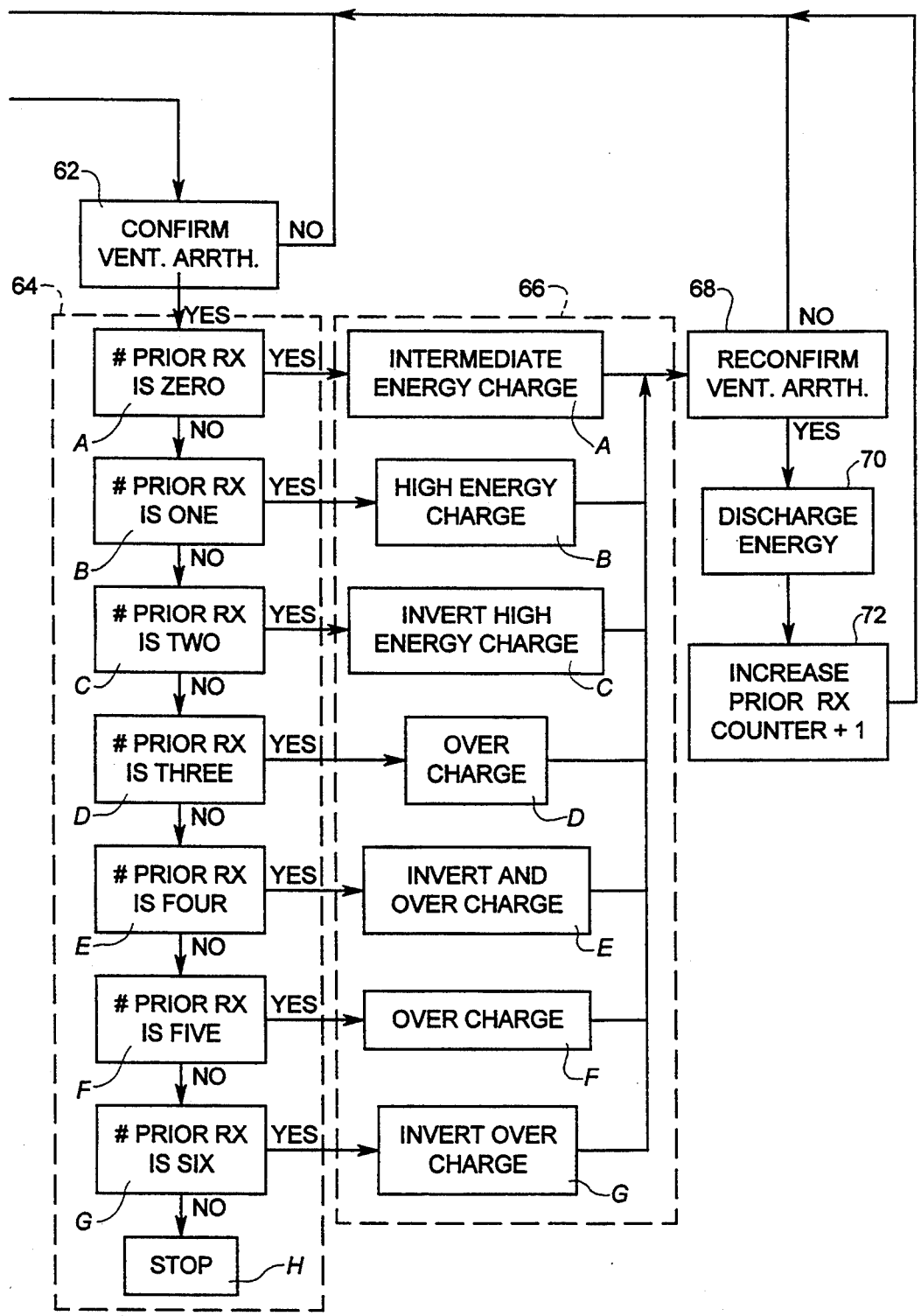

FIG. 4 depicts a more involved flow diagram of an additional embodiment of the present invention. The method steps of FIG. 4 take into account the variations in treatment for the different ventricular arrhythmias. Beginning with step 30 the present invention is in a monitoring mode. Upon detection of a possible ventricular arrhythmia, function is passed to step 32. As in FIG. 3, there is present in FIG. 4 a step 34 to reset the prior treatment attempt counter to zero if no ventricular arrhythmia is detected. However, if step 32 returns a logical "yes", the system then determines which ventricular arrhythmia has been detected passing functions sequentially through steps 56, 58, and 60 with step 56 determining the presence of ventricular fibrillation. If ventricular fibrillation is detected, function is passed to step 62 to confirm the presence of the ventricular arrhythmia. If it is determined that a ventricular arrhythmia does not exist, function is passed to step 32. If there is no detection of ventricular arrhythmia, function passes through step 34 back to the monitoring step 30.

If step 62 confirms the presence of ventricular arrhythmia in the form of ventricular fibrillation, function passes to step 64 which in general determines the number of prior treatment counts. As shown in FIG. 4, step 64 is divided into eight logical steps lettered A through H corresponding to the count on the prior treatment attempt counter.

For the treatment of ventricular fibrillation, step 64A would determine that the prior treatment counter is zero and pass function to step 66A the corresponding charging step to determine that this is the first electrical countershock and a lowered or intermediate energy charge is to be used. This lowered energy charge usually is in a range of about 600 volts. Once charging step 66 is complete, function is passed to step 68 for reconfirmation of the ventricular arrhythmia. If a logical "no" is returned, function is passed back to step 34 as above. However, if reconfirmation step 68 returns a logical "yes", function passes to step 70 and the electrical countershock is delivered to the myocardium. Following the countershock the prior treatment attempt counter is increased by one at step 72 and function is return to step 32.

As is readily apparent from FIG. 4, if there is treatment failure, the ICD system once again will go from detection step 32 to a determination if there is ventricular fibrillation in step 56, confirmation of a ventricular arrhythmia in step 62, and determination of the number of prior treatment attempts at step 64. Prior treatment determination step 64B leads to charging step 66B which allows the system to charge at the maximum rated voltage specified for the system. Step 64C leads to step 66C which calls for the maximum rated specified voltage but in an inverted mode. Charging step 66C provides that the polarity of the discharge electrodes is to be reversed. This electrode polarity inverting is accomplished through switching steps that are not depicted. For a more detailed discussion of how the inverted configuration therapy regimen of this embodiment is achieved, reference is made to the previously-identified co-pending application entitled SUCCESSIVE CHANGEABLE WAVEFORMS. Steps 64F to 66F repeat the treatment of 64D to 66D. The reasoning behind inverting the electrode polarity is that because the previous high energy discharge was unsuccessful there is little reason to repeat an unsuccessful step. Step 64D provides for charging step 66D which is an overcharge step.

Compared to FIG. 3, FIG. 4 differs from FIG. 3 in an approach to treatment of ventricular fibrillation by providing for an overcharge countershock after only three countershock failures. The reasoning for this is similar to the reasoning for inverting the high energy countershock in the previous step. If an intermediate energy countershock, a high energy countershock, and an inverted high energy countershock have all failed to successfully defibrillate the myocardium, then it makes no sense to repeat any one of these three treatment modalities. Logic would dictate that the fourth shock which comes at more than one minute after the onset of ventricular fibrillation ought to be an overcharge electrical countershock. Steps 64E to 66E undertake an inverted configuration with an overcharged system with the understanding that the previous four attempts have all failed.

The preferred embodiment of ICD 217 of the present invention uses smaller capacitors that store less energy, the charging time is significantly less than the charging times of existing devices. Thus, treatment cycles 64F and 64G to the corresponding 66F and 66G also can be accomplished within a three minute period prior to the onset of brain damage in the patient. In the preferred embodiment shown in FIGS. 10–14, ICD 217 is capable of charging capacitors 226 and 227 in less than about 10 seconds and, more typically, in less than about 8 seconds. Thus, the total cycle time for detection, charging, verification, delivery and re-detection is only about 20 to 25 seconds. Finally, step 64H contemplates that all prior treatment attempts have failed and stops the device.

Returning to logical step 32, upon detection of a ventricular arrhythmia. If it is determined through step 58 that a high rate ventricular tachycardia is present, function is passed to step 74 for confirmation of the presence of that ventricular arrhythmia. If it is determined that a high rate ventricular tachycardia is present, function is then passed to step 76 to determine the number of prior treatments. Depending upon the number of prior treatments in step 76, function is then passed to a corresponding charging step 78 much as it did for steps 64 and 66 under the treatment for ventricular fibrillation.

Treatment for ventricular tachycardia is approached in a less vigorous fashion than it is for ventricular fibrillation because the organized electrical activity of ventricular tachycardia is more sensitive to electrical countershock intervention. Two adaptations specific for treatment of ventricular tachycardia are found in steps 78A, 78B, 78C, and step 80. With a return of a logical "yes" from step 76A, step 78A provides for an intermediate energy charge in the range of approximately 600 volts to the capacitors. When charging is complete, function is then passed to a synchronization step 80 which allows for synchronization of the discharge with an R wave from the ventricular tachycardia. The synchronization prevents inadvertent electrical countershock therapy occurring at a T wave when the ventricles are the most susceptible to triggering of ventricular fibrillation. Once the system has synchronized with an R wave, reconfirmation of the ventricular arrhythmia occurs with step 82. If reconfirmed, step 84 allows for discharge of the electrical countershock in synchronization with an R wave. The prior treatment counter is increased by one in step 86 and function is returned to step 32. If there is treatment failure for the high rate ventricular tachycardia, function of the present invention passes through the appropriate steps 58 to 74 to 76. Step 76B provides a high energy charge to the capacitors at step 78B which is then synchronized with an R wave at step 80. With reconfirmation step 82 and discharge at step 84 the counter is increased by one in step 86. If the treatment is unsuccessful, the present invention returns through the appropriate steps to step 76C which allows for a high energy charge but will invert the polarity of the electrodes at step 78C. Once charged, the system is synchronized at step 80 and passes through steps 82, 84 and 86.

If the treatment continues to be unsuccessful, the system returns to steps 76D, 76E, 76F, and 76G in succession and these steps correspond with steps 64B, 64C, 64D, and 64E for the treatment of ventricular fibrillation. High rate ventricular tachycardia, much like ventricular fibrillation, becomes increasingly resistent to electrical countershock therapy as time progresses from onset of the ventricular arrhythmia. Therefore, by the time the system has reached step 76F nearly three minutes has transpired since the onset of ventricular arrhythmia and all prior attempts at treatment with both high energy synchronized and high energy unsynchronized as well as concomitant inverted polarity of the electrodes has failed. Repeating these prior steps would have little likelihood of success and therefore method step 76F and 76G to step 78F and 78G provide for overcharging the capacitor storage system as the last attempts to cardiovert the high rate ventricular tachycardia. If unsuccessful, step 76H stops the device.

Following each electrical countershock from step 84 through 86 function is returned to step 32. If at any time the ICD system were to determine that instead of high rate ventricular tachycardia, the arrhythmia had deteriorated to a ventricular fibrillation, function could then pass to steps 62 through 64. If the two preceding countershock attempts had been for high rate ventricular tachycardia, the prior treatment attempt counter would be at 2 on the next passage. If step 32 determined the presence of a ventricular arrhythmia and instead step 56 determines that it is ventricular fibrillation which is confirmed at step 62, then upon reaching step 64C function would pass to step 64C skipping the first two treatment modalities for ventricular fibrillation. Logically this makes sense because there had already been two previous attempts to electrically cardiovert the myocardium and circumstances are deteriorating having gone from high rate ventricular tachycardia to ventricular fibrillation. There would be no logical reason to begin with a lower energy step 64A to step 66A. Step 64C will allow the system to undergo a high energy charge, invert the electrode configuration and give an unsynchronized discharge at step 70 following a reconfirmation at step 68.

The treatment for low rate ventricular tachycardia is less aggressive than the approach for high rate ventricular tachycardia. Low rate ventricular tachycardia is determined at step 60 with function passing to step 88. With confirmation of the ventricular arrhythmia, function is passed to step 90 to determine the prior treatment attempt count in order to determine what level of charge to place on the capacitor system. For the first two attempts, steps 90A and 90B pass function to step 92A which calls for a low energy charge in approximately the 450 volt range. Low rate ventricular tachycardia is particularly sensitive to electrical countershock therapy and responds readily to the lower energy. Once charged through step 92A, function is passed to 94 for synchronization with an R wave. Step 96 carries out a reconfirmation of the ventricular arrhythmia then function passes to discharge step 98 and the electrical energy is delivered to the myocardium. The prior treatment counter is increased by one at step 100 and function returns to step 32.

As in the treatment for ventricular fibrillation and high rate ventricular tachycardia, step 90 corresponding to step 76 will determine the count on the prior treatment attempt counter to determine which level of charge and electrode polarity to choose in step 92. Charging step 92B provides for an intermediate or approximately 600 volt charge to be delivered by synchronized step 94. Step 92C provides for inversion of electrode polarity and to deliver a synchronized intermediate energy countershock. Steps 92D and 92E provide for the high energy approximately 750 volt energy charge with 92D delivering it in the normal polarity and 92E inverting the electrode polarity. Steps 92A through 92E treatment modalities are all synchronized with the R wave. If the treatment continues to fail in cardioverting the myocardium, steps 92F through 92J increase the level of aggressive treatment beginning with unsynchronized high energy charging at step 92F and beginning overcharging at step 92H. The last treatment is carried out through step 90J leading to the step of overcharging and inverting the electrode polarity. By the time the system has arrived at step 90J, upwards of five minutes has elapsed since the onset of the ventricular arrhythmia. If step 90J and its subsequent overcharge countershock fails, step 90K provides for stopping the device with an understanding that the myocardium is resistent to electrical countershock measures.

As in high rate ventricular tachycardia, the low rate ventricular tachycardia method steps provide for shifting to high rate ventricular tachycardia treatment or ventricular fibrillation treatment at any time steps 32 through 56 and 58 determine that these more severe forms of ventricular arrhythrnia exist. As noted above, the system will skip to the appropriate method step corresponding with the number on the prior treatment counter.

The method depicted in FIG. 4 is for automatic ICD treatment of ventricular arrhythmia. A persistent detection of a ventricular arrhythmia at step 32 may also be the result of a false perception of ventricular arrhythmia. Such false positive detections may be due to background noise or incorrect interpretation of a supraventricular arrhythmia. For a more detailed discussion of arrhythmia detection, reference is made to the copending application entitled FIBRILLATION AND TACHYCARDIA DETECTION, Ser. No. 07/848,147 assigned to the assignee of the present invention.

Alternatively, a mechanism can be provided to the patient to allow the patient to manually interrupt the ICD's function. This is particularly useful in those circumstances where the ICD is erroneously charging in order to treat background noise. In such circumstances, the patient will become aware of the ICD charging, but the patient will feel fine since cardiac function is not impaired. At that time the patient will make the determination to manually interrupt the ICD. Alternatively, the patient may choose to interrupt a proper sequence on the basis that the patient is tolerating the arrhythmia and since the patient is conscious, wishes to forego a painful countershock. One method of manual interruption of an ICD is to incorporate an interrupt circuit and method step responsive to a strong magnetic field from a hand held magnet placed over the skin covering the ICD.

FIG. 5 depicts a time line of the treatment sequence for treating low rate ventricular tachycardia. Discharge pulses 110 correspond to the two consecutive electrical countershock therapies delivered at step 92A in FIG. 4. As noted in FIG. 5, countershock pulses 110 are approximately 450 volts. Countershock pulse 112 is an intermediate, normal polarity countershock pulse with countershock pulse 114 being its counterpart depicting the reverse polarity of the discharge electrodes. Beginning with countershock 116, the system discharges the countershock at the maximum rate specified for the system. Discharge wave 118 is the corresponding inverted electrode polarity countershock to 116. Discharge waves 120 and 122 correspond to repeats of 116 and 118 with discharge waves 124 and 126 representing overcharge countershocks as the terminal sequence in the treatment path for treating low rate ventricular tachycardia. Note that discharge wave 126 arrives at approximately the six minute mark after onset of the ventricular arrhythmia.

FIG. 6 is a treatment sequence for the high rate ventricular tachycardia as depicted from FIG. 4. This depiction begins with countershock wave 128 at an intermediate level and following up with countershock waves 130 through 136 at maximum specified rate alternately inverting the electrode polarity. Countershock waves 138 and 140 represent the overcharge terminal sequence arriving at approximately the four minute mark.

FIG. 7 represents the treatment sequence for treating ventricular fibrillation with the initial countershock wave 142 being of intermediate voltage but immediately jumping to maximum specified voltage at countershock wave 144 and inverting the maximum discharge with countershock wave 146. Recognizing the severity and urgency associated with ventricular fibrillation, the present embodiment overcharges at countershock wave 148 at approximately the two minute mark and carries out a succession of four overcharge countershock attempts before terminating treatment at approximately the four minute mark.

Figure 8:
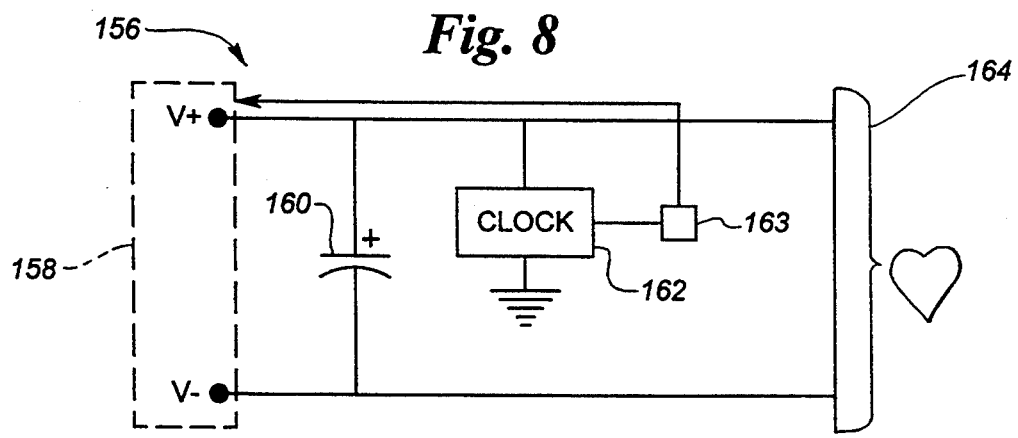
FIG. 8 is a schematic diagram of the present invention using a clock to control the charge timing.

FIG. 8 depicts a general electrical schematic of an embodiment 156 for the present invention utilizing a clock 162 to time the charging sequence for high voltage capacitor 160. This system works on the principal that the power rate of charging capacitor 160 is a known constant based on the current and voltage delivered by high voltage supply 158. Clock 162 is capable of timing to allow for low, intermediate, high, and overcharge energies to high voltage capacitor 160, depending upon the treatment called for by the method step. When clock 162 has reached its end point a signal is then passed to charge enable 163 which feeds back to power supply 158 turning off the voltage charge to capacitor 160. Discharge subdevice 164 represents the switching and electrode configurations in a general schematic sense and delivering the stored energy from capacitor 160 to the myocardium.

Figure 9:
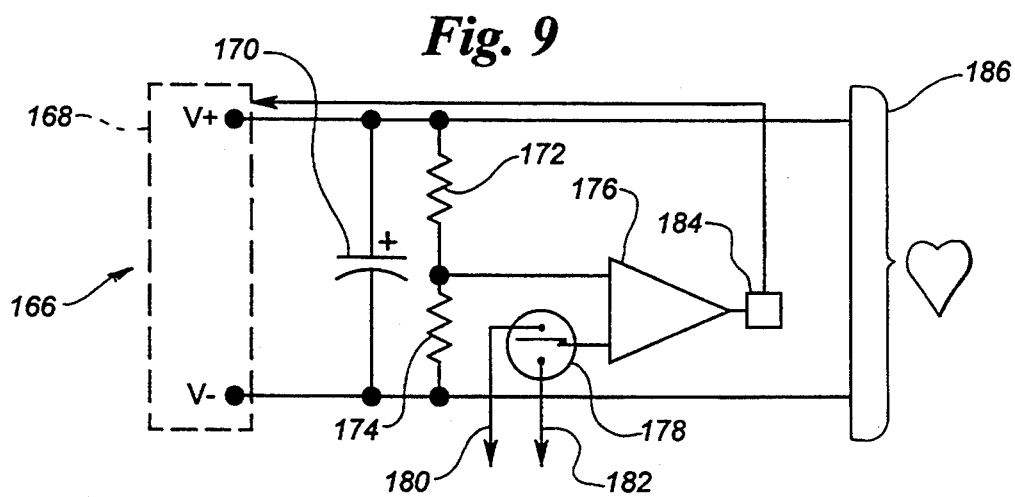
FIG. 9 is a schematic diagram of the present invention depicting an additional embodiment for monitoring the charge voltage.

FIG. 9 represents a schematic diagram of an additional embodiment 166 of the present invention utilizing direct voltage comparisons to determine the charging end point. Power supply 168 provides the charging voltage for charging capacitor 170. Resistor 172 in conjunction with resistor 174 provides a voltage divider to determine the actual voltage across capacitor 170. Comparator 176 monitors the voltage divider at a point between resister 172 and 174 and through switch 178 compares the voltage from the voltage divider circuit to a reference voltage 180 or an overcharge voltage reference 182. Alternatively, comparator 176 can switch back and forth from reference 180 to reference 182 to determine the monotonic derivative decay of the voltage charge to determine the end point for overcharging based on a decaying first derivative of the rate of charging of capacitor 170. When comparator 176 has determined that the level of voltage called for has been reached, a signal is passed to charging enabler 184 which feeds back on power supply 168 discontinuing charge of capacitor 170. Switching and electrode means 186 then delivers the electrical countershock to the myocardium.

Figure 10:
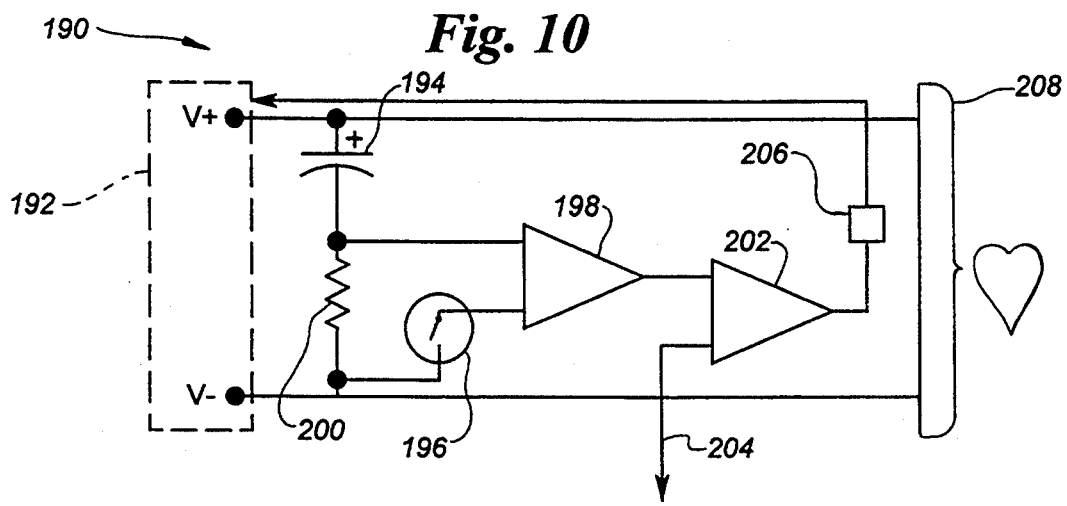
FIG. 10 is a schematic diagram of the present invention depicting an additional embodiment for determining the charging end point.

FIG. 10 depicts a schematic diagram of another additional embodiment 190 of the present invention utilizing another direct voltage comparison to determine the charging end point. Power supply 192 provides the charging voltage for charging capacitor 194. Power supply 192 is capable of repeated, momentary interruptions in the charging of capacitor 194 during which time switch 196 briefly closes allowing comparator 198 to measure the voltage across resistor 200. The output of comparator 198 is passed to differential amplifier 202 which then compares the measured voltage to a reference voltage supplied by lead 204. Switch 196 then opens and power supply 192 continues charging. This sequence is repeated until charging has brought the voltage across resistor 200 equal to the reference voltage. This voltage is proportional to the leakage current through capacitor 194. When comparator 198 has determined that the level of leakage current called for has been reached, a signal is passed to charging enabler 206 which signals power supply 192 to discontinue charging of capacitor 194. Switching and electrode means 208 then delivers the electrical countershock to the myocardium.

For example, the leakage current through a nominal maximum 750 volt capacitor bank may be 10 μA at 750 volts. However, at 850 volts, the current may exceed 100 μA, at which point charging would cease.

The present invention utilizes an overcharging principal which takes advantage of aluminum oxide electrolytic capacitor technology in order to safely achieve an overcharge of an electrolytic capacitor without catastrophic breakdown. The benefits of providing overcharging are several fold. The first is the ability to provide additional energy to a countershock in those circumstances where lesser energy has already failed to achieve defibrillation or cardioversion. There is no sense in repeating steps that have already proven their inability to effect treatment. Alternatively, overcharging capabilities allow for utilizing 10% to 25% smaller capacitors because the overcharging capability is able to pack in the equivalent amount of energy into the smaller capacitor as the significantly larger capacitors store at the lower voltage. Finally, reduction in size allows for placement of ICD systems in more convenient anatomic locations within the human body. Any combination of overcharging and size reduction will yield beneficial gains in providing a cardioverting defibrillating system.

We claim:

1. A method for operating an implantable cardioverter defibrillator device electrically connected to two or more implanted discharge electrodes located in a human patient to treat myocardial fibrillation, the method comprising the device implemented steps of:
   a) sensing for a myocardial fibrillation in a human patient;
   b) charging a capacitive charge storage system at least once to a voltage value at or below a nominal maximum voltage in response to sensing the myocardial fibrillation;
   c) discharging the capacitive charge storage system through the two or more implanted discharge electrodes;
   d) recharging the capacitive charge storage system at least once to an overcharged voltage in excess of the nominal maximum voltage in response to a sensing of a persistent myocardial fibrillation which the at least one discharge according to step (c) failed to treat; and
   e) discharging the capacitive charge storage system through the two or more implanted discharge electrodes to effect a final treatment for the myocardial fibrillation.

2. The method of claim 1 wherein the maximum nominal voltage is a maximum programmable voltage specified for the device.

3. The method of claim 1 wherein the maximum nominal voltage is a maximum manufacturer's rated charging voltage for the capacitive charge storage system.

4. The method of claim 1 wherein the capacitive charge storage system is a pair of electrolytic capacitors in series and the maximum nominal voltage is a maximum charging voltage across the electrolytic capacitors of greater than 375 volts across each capacitor.

5. A method for operating an implantable cardioverter defibrillator device electrically connected to two or more implanted discharge electrodes located in a human patient to treat myocardial fibrillation, the method comprising the device implemented steps of:
   a) sensing for myocardial fibrillation in the human patient;
   b) charging a capacitive charge storage system at least once to a maximum nominal voltage in response to sensing a myocardial fibrillation;
   c) discharging the capacitive charge storage system through the two or more implanted discharge electrodes to effect treatment of the myocardial fibrillation;
   d) reverting immediately to sensing for myocardial fibrillation;
   e) repeating steps (b)–(d) a first predetermined number of times if step (d) senses a failure to treat the myocardial fibrillation;
   f) switching to an overcharged voltage operation if step (d) senses a failure to treat the myocardial fibrillation and the first predetermined number of times have been exceeded;
   g) overcharging the capacitive charge storage system beyond the maximum nominal voltage;
   h) discharging the overcharged capacitive charge storage system through the two or more implanted discharge electrodes to effect a final treatment of the myocardial fibrillation;
   i) reverting immediately to sensing for myocardial fibrillation;
   j) repeating steps (f)–(h) a second predetermined number of times if step (i) senses a persistent failure to treat the myocardial fibrillation; and
   k) stopping all myocardial fibrillation treatment efforts after the second predetermined number of times have been exceeded without success in treating the myocardial fibrillation.

6. The method of claim 5 in which the first predetermined number of treatment attempts is less than six.

7. The method of claim 5 in which the second predetermined number of treatment attempts using overcharged voltage is less than four.

8. An implantable cardioverter defibrillator apparatus electrically connected to two or more implanted discharge electrodes adapted to be located in a human patient for treating myocardial arrhythmias comprising:
   a) sensing means for sensing a myocardial arrhythmia in the human patient;

b) capacitive charge storage means electrically connected to the two or more implanted electrodes for storing an electrical charge;

c) power source means for charging the capacitive charge storage means to a charging voltage;

d) control means for selectively controlling the power source means and the capacitive charge storage means in response to the sensing of the myocardial arrhythmia in order to deliver at least one electrical countershock to the two or more electrodes in accordance with a programmable therapy regimen stored in the apparatus, the control means including:

d0) means for storing the programmable therapy regimen;

d1) means for regulating a charging voltage applied by the power source means to the capacitive charge storage means in response to a charging voltage value indicated in the programmable therapy regimen;

d2) means for selectively discharging the capacitive charge storage means as an electrical countershock in response to a reconfirmed sensing of the myocardial fibrillation by the sensing means;

d3) means for counting a successive number of failed electrical countershocks in the programmable therapy regimen when the sensing means determines that the electrical countershock was not successful in treating the myocardial fibrillation; and d4) means for resetting the means for counting to zero after a successful treatment of the myocardial fibrillation, wherein at least one of the voltages in the programmable therapy regimen is a maximum nominal voltage and at least another of the voltages in the programmable therapy regimen is an overcharged voltage greater than the maximum voltage.

9. The apparatus of claim 8 wherein the maximum nominal voltage is a maximum programmable voltage specified for the apparatus.

10. The apparatus of claim 8 wherein the maximum nominal voltage is a maximum manufacturer's rated charging voltage for the capacitive charge storage system.

11. The apparatus of claim 8 wherein the capacitive charge storage system is a pair of electrolytic capacitors in series and the maximum voltage is a maximum charging voltage across the electrolytic capacitors of greater than 375 volts across each capacitor.

12. The apparatus of claim 8 wherein the programmable therapy regimen comprises a series of charging voltage values corresponding to at least three electrical countershocks, including:

a first charging voltage value that is less than the maximum voltage;

a second charging voltage value that is equal to the maximum voltage; and a third charging voltage value that is greater than or equal to the overcharged voltage.

13. The apparatus of claim 12 wherein the programmable therapy regimen includes two or more second charging voltage values, each second charging voltage value further specifying a unique discharge pathway among the two or more electrodes through which the electrical countershock will be discharged.

14. A method for operating an implantable cardioverter defibrillator device electrically connected to two or more implanted discharge electrodes located in a human patient to treat myocardial high rate ventricular tachycardia, the method comprising the device implemented steps of:

a) sensing for a myocardial high rate ventricular tachycardia in a human patient;

b) charging a capacitive charge storage system at least once to a voltage value below a nominal maximum voltage in response to sensing the myocardial high rate ventricular tachycardia;

c) discharging the capacitive charge storage system in synchrony with an R wave through the two or more implanted discharge electrodes;

d) recharging the capacitive charge storage system at least once to a voltage value at the nominal maximum voltage in response to a sensing of a persistent myocardial high rate ventricular tachycardia which the at least one discharge according to step (c) failed to treat;

e) discharging the capacitive charge storage system in synchrony with an R wave through the two or more implanted discharge electrodes;

f) recharging the capacitive charge storage system at least once to a voltage value at the nominal maximum voltage in response to a sensing of a persistent myocardial high rate ventricular tachycardia which the at least one discharge according to step (e) failed to treat;

g) discharging the capacitive charge storage system asynchronously through the two or more implanted discharge electrodes;

h) recharging the capacitive charge storage system at least once to an overcharged voltage value in excess of the nominal maximum voltage in response to a sensing of a persistent myocardial high rate ventricular tachycardia which the at least one discharge according to step (g) failed to treat; and i) discharging the capacitive charge storage system asynchronously through the two or more implanted discharge electrodes.

15. The method of claim 14 further comprising after step (e) the steps of:

e1) recharging the capacitive charge storage system at least once to a voltage value at the nominal maximum voltage in response to a sensing of a persistent myocardial high rate ventricular tachycardia which the at least one discharge according to step (e) failed to treat; and e2) discharging the capacitive charge storage system in synchrony with an R wave through the two or more implanted discharge electrodes with inverted polarity.

16. The method of claim 14 further comprising after step (g) the steps of:

g1) recharging the capacitive charge storage system at least once to a voltage value at the nominal maximum voltage in response to a sensing of a persistent myocardial high rate ventricular tachycardia which the at least one discharge according to step (g) failed to treat; and g2) discharging the capacitive charge storage system asynchronously through the two or more implanted discharge electrodes with inverted polarity.

17. The method of claim 14 further comprising after step (i) the steps of:

i1) recharging the capacitive charge storage system at least once to an overcharged voltage value in excess of the nominal maximum voltage in response to a sensing of a persistent myocardial high rate ventricular tachycardia which the at least one discharge according to step (i) failed to treat; and i2) discharging the capacitive charge storage system through the two or more implanted discharge electrodes with inverted polarity to effect a final treatment for the persistent myocardial high rate ventricular tachycardia.

18. The method of claim 14 wherein the maximum nominal voltage is a maximum programmable voltage specified for the device.

19. The method of claim 14 wherein the below nominal voltage is a programmable voltage at about 600 volts specified for the device.

20. The method of claim 14 wherein the maximum nominal voltage is a maximum manufacturer's rated charging voltage for the capacitive charge storage system.

21. The method of claim 14 wherein the capacitive charge storage system is a pair of electrolytic capacitors in series and the maximum nominal voltage is a maximum charging voltage across the electrolytic capacitors of greater than 375 volts across each capacitor.

22. A method for operating an implantable cardioverter defibrillator device electrically connected to two or more implanted discharge electrodes located in a human patient to treat myocardial low rate ventricular tachycardia, the method comprising the device implemented steps of:
  a) sensing for a myocardial low rate ventricular tachycardia in a human patient;
  b) charging a capacitive charge storage system at least once to a voltage value below a nominal maximum voltage in response to sensing the myocardial low rate ventricular tachycardia;
  c) discharging the capacitive charge storage system in synchrony with an R wave through the two or more implanted discharge electrodes;
  d) recharging the capacitive charge storage system at least once to a voltage value at the nominal maximum voltage in response to a sensing of a persistent myocardial low rate ventricular tachycardia which the at least one discharge according to step (c) failed to treat;
  e) discharging the capacitive charge storage system in synchrony with an R wave through the two or more implanted discharge electrodes;
  f) recharging the capacitive charge storage system at least once to a voltage value at the nominal maximum voltage in response to a sensing of a persistent myocardial low rate ventricular tachycardia which the at least one discharge according to step (e) failed to treat;
  g) discharging the capacitive charge storage system asynchronously through the two or more implanted discharge electrodes;
  h) recharging the capacitive charge storage system at least once to an overcharged voltage value in excess of the nominal maximum voltage in response to a sensing of a persistent myocardial low rate ventricular tachycardia which the at least one discharge according to step (g) failed to treat; and
  i) discharging the capacitive charge storage system asynchronously through the two or more implanted discharge electrodes.

23. The method of claim 22 further comprising after step (c) the steps of:
  c1) recharging a capacitive charge storage system at least once to a voltage value below a nominal maximum voltage in response to sensing the myocardial low rate ventricular tachycardia which the at least one discharge according to step (c) failed to treat; and
  c2) discharging the capacitive charge storage system in synchrony with an R wave through the two or more implanted discharge electrodes with inverted polarity.

24. The method of claim 22 further comprising after step (e) the steps of:
  e1) recharging the capacitive charge storage system at least once to a voltage value at the nominal maximum voltage in response to a sensing of a persistent myocardial low rate ventricular tachycardia which the at least one discharge according to step (e) failed to treat; and
  e2) discharging the capacitive charge storage system in synchrony with an R wave through the two or more implanted discharge electrodes with inverted polarity.

25. The method of claim 22 further comprising after step (g) the steps of:
  g1) recharging the capacitive charge storage system at least once to a voltage value at the nominal maximum voltage in response to a sensing of a persistent myocardial low rate ventricular tachycardia which the at least one discharge according to step (g) failed to treat; and
  g2) discharging the capacitive charge storage system asynchronously through the two or more implanted discharge electrodes with inverted polarity.

26. The method of claim 22 further comprising after step (i) the steps of:
  i1) recharging the capacitive charge storage system at least once to an overcharged voltage value in excess of the nominal maximum voltage in response to a sensing of a persistent myocardial low rate ventricular tachycardia which the at least one discharge according to step (i) failed to treat; and
  i2) discharging the capacitive charge storage system through the two or more implanted discharge electrodes with inverted polarity to effect a final treatment for the persistent myocardial low rate ventricular tachycardia.

27. The method of claim 22 wherein the maximum nominal voltage is a maximum programmable voltage specified for the device.

28. The method of claim 22 wherein the maximum nominal voltage is a maximum manufacturer's rated charging voltage for the capacitive charge storage system.

29. The method of claim 22 wherein the below nominal voltage is a programmable voltage at about 450 volts specified for the device.

30. The method of claim 22 wherein the below nominal voltage is a programmable voltage at about 600 volts specified for the device.

31. The method of claim 22 wherein the capacitive charge storage system is a pair of electrolytic capacitors in series and the maximum nominal voltage is a maximum charging voltage across the electrolytic capacitors of greater than 375 volts across each capacitor.

* * * * *